United States Patent [19]

Eckels et al.

[11] Patent Number: 4,834,645
[45] Date of Patent: May 30, 1989

[54] METHOD AND APPARATUS FOR TRANSPORT, INTRODUCTION, ATOMIZATION AND EXCITATION OF EMISSION SPECTRUM FOR QUANTITATIVE ANALYSIS OF HIGH TEMPERATURE GAS SAMPLE STREAMS CONTAINING VAPOR AND PARTICULATES WITHOUT DEGRADATION OF SAMPLE STREAM TEMPERATURE

[75] Inventors: David E. Eckels, Ankeny; William J. Hass, Ames, both of Iowa

[73] Assignee: Iowa State University Research Foundation, Inc., Ames, Iowa

[21] Appl. No.: 165,141

[22] Filed: Mar. 7, 1988

[51] Int. Cl.⁴ .................................................. F23J 7/00
[52] U.S. Cl. ............................................ 431/4; 431/8; 431/126; 431/284; 356/315
[58] Field of Search ............... 431/154, 155, 156, 157, 431/188, 184, 284, 353, 126, 207, 288, 253, 278, 202, 4, 8; 250/218; 356/315

[56] References Cited

U.S. PATENT DOCUMENTS

| 399,770 | 3/1889 | Meyers | 431/207 |
|---|---|---|---|
| 1,829,001 | 10/1931 | Geromanos | 356/315 |
| 2,735,285 | 2/1956 | Ferleger | 431/288 |
| 2,990,748 | 7/1961 | Vallee et al. | 431/126 |
| 2,990,749 | 7/1961 | Thiers et al. | 431/126 |
| 3,529,913 | 9/1970 | Venghiattis | 431/253 |
| 3,644,743 | 2/1972 | Binek et al. | 250/218 |
| 3,730,673 | 5/1973 | Straitz, III | 431/278 |
| 3,748,080 | 7/1973 | Dunn | 431/4 |
| 3,801,261 | 4/1974 | Reed et al. | 431/202 |
| 4,726,763 | 2/1988 | Newman | 431/353 |

FOREIGN PATENT DOCUMENTS 681356 6/1977 U.S.S.R. .

Primary Examiner—James C. Yeung
Attorney, Agent, or Firm—Zarley, McKee, Thomte, Voorhees & Sease

[57] ABSTRACT

A sample transport, sample introduction, and flame excitation system for spectrometric analysis of high temperature gas streams which eliminates degradation of the sample stream by condensation losses.

13 Claims, 1 Drawing Sheet

METHOD AND APPARATUS FOR TRANSPORT, INTRODUCTION, ATOMIZATION AND EXCITATION OF EMISSION SPECTRUM FOR QUANTITATIVE ANALYSIS OF HIGH TEMPERATURE GAS SAMPLE STREAMS CONTAINING VAPOR AND PARTICULATES WITHOUT DEGRADATION OF SAMPLE STREAM TEMPERATURE

GRANT REFERENCE

The United States government may have certain rights in this invention. The invention described herein was made in the course of performance under a contract with the United States Department of Energy.

BACKGROUND OF THE INVENTION

This invention relates generally to the transport, introduction, atomization, and excitation of the constituents of elevated temperature sample streams whose chemical compositions are to be determined by spectrometric techniques; more specifically, to the transport, introduction, atomization, and excitation of the emission spectra of the constituents of elevated temperature sample streams whose sodium and potassium concentrations are to be determined and monitored continuously by flame emission spectrometric techniques.

In energy generation schemes in which hot gas product streams derived from the combustion or gasification of coal are ultimately used to drive turbine-generator assemblies, determination and continuous monitoring of the concentrations of sodium and potassium that are present in the gas streams is important for characterization and monitoring of the performance of hot gas cleanup equipment and processes. Minimization of turbine corrosion is one of the principal goals of the hot gas cleanup operation. The important concentrations are: vapor-borne sodium, particulate-borne sodium, vapor-borne potassium, and particulate-borne potassium. The concentrations of importance are those which prevail at actual process operating temperatures and pressures.

Flame spectrometric methods have been shown to have sufficient detecting power, accuracy, and precision for such determinations and, when combined with appropriate means for continuous introduction of a representative sample of a gas stream of interest, can provide continuous concentration monitoring. For accuracy, avoidance of the loss of alkalicontaining materials by condensation of vapor prior to introduction of the sample stream into the atomization/excitation cell is a critical requirement.

It can therefore be seen that, particularly where there is use of gas turbines in systems fueled by coal or coal derived fuels, there is a continuing need for monitoring alkali-containing materials, particularly. The process stream portions that are of primary interest with respect to alkali monitoring are (1) the turbine input gas stream for characterization of the alkali portion of the corrosive atmosphere to which the turbine components will be exposed, and (2) the inputs and outputs of hot gas cleanup devices for determination and online monitoring of the efficiency of trial systems.

This invention has as a primary objective the development of a method and apparatus for excitation of the emission spectrum of a flowing representative sample of hot gas, with continuous monitoring of the spectrum to be employed for online determination of sodium and potassium concentrations in gaseous fuels produced from coal and in hot flue gas from combustion of coal and/or other fuels produced from coal.

Another object of the invention is to provide an apparatus which utilizes the momentum of an elevated temperature sample stream exiting from a heat traced and thermally insulated sample transport/sample introduction tube for introduction of vapor and (liquid and/or solid) particulate constituents of the sample stream, without temperature degradation, into the axial channel of a flame atomization/excitation cell for subsequent analysis of the materials present in the sample stream by spectrometric methods.

A still further object of the invention is to provide an apparatus which employs heat tracing and appropriate thermal insulation materials with the sample transport/sample introduction tube so that vapor state material which enters that tube remains in the vapor state during its transit of the tube and enters the axial channel of the flame atomization/excitation cell as vapor state material.

A yet further object of the invention is to provide an apparatus which produces a flame atomization/excitation cell in a manner that provides superior accessibility for the introduction of material into the axial channel of the flame atomization/excitation cell.

Another object of the invention is to provide an apparatus which produces a flame atomization/excitation cell with a high degree of accessibility for the direct introduction of material into the axial channel of the flame atomization/excitation cell, and sufficient working space immediately below the flame atomization/excitation cell to allow the generation of vapor, liquid, or aerosol streams from solids, liquids, solutions, slurries, powders, or corrosive materials and direct introduction of such streams into the axial channel of the flame atomization/excitation cell.

SUMMARY OF THE INVENTION

A sample transport, introduction, and flame excitation system specifically designed for spectrometric analysis of hot gas sample streams and the avoidance of sample stream degradation by condensation losses, so that spectral characterizations obtained are in fact true results for the sample stream. The system comprises a manifold for supply of pre-mixed fuel gas and oxidizing gas, with the manifold being connected to at least two burner nozzles, and a heated and thermally insulated sample transport and sample introduction tube. The burner nozzles are symmetrically positioned around the axis of the sample transport/sample introduction tube and provide a confluence of angularly disposed flames to receive and excite the sample stream immediately upon exit from the sample tube.

DETAILED DESCRIPTION OF THE INVENTION

The apparatus of this invention, referred to generally at 10, provides a spectral flame excitation system which provides high temperature gas stream for spectral analysis without degradation of the sample stream by condensation losses. The burner assembly consists of a plurality of commercially available burner nozzles 12, 14, 16 and 18, respectively, arranged on a square base manifold 20 which provides a common supply manifold for the flow of pre-mixed fuel gas and oxidant gas mixture from supply line 22 via conduits 24, 26, 28 and 30, such that fuel gas-oxidant mixture is supplied to nozzles 12, 14, 16 and 18, respectively. As those skilled in the art know, the common combustion gas used is a mixture of propane and oxygen. Centrally positioned with respect to previously referred-to burner nozzles 12-18 is a sample transport/sample introduction tube 32 which may, for example, be a stainless steel tube having an outside diameter of 0.635 cm. This sample tube 32 is preferably electrically heat traced and is preferably wrapped with ceramic fiber insulation (See FIG. 3) in order to prevent vapor condensation.

Figure 1:
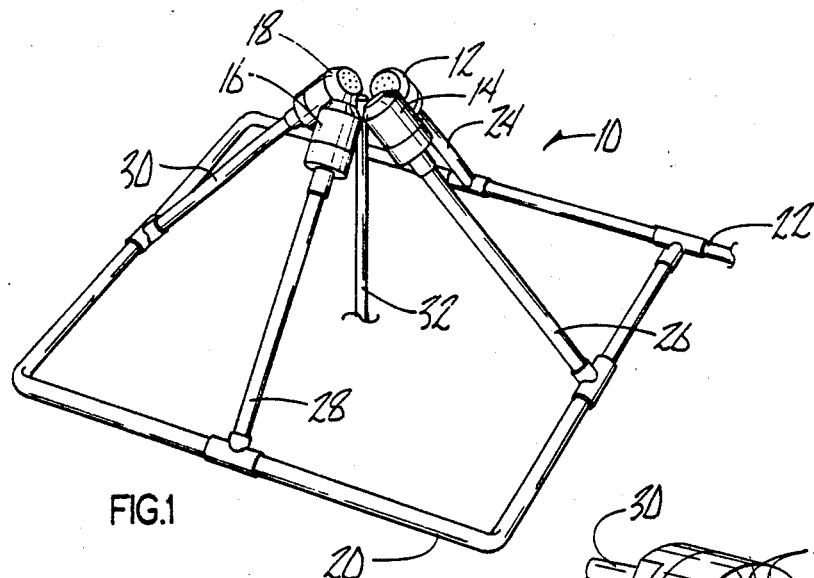
FIG. 1 is a perspective view of the spectral flame burner system of this invention with the electrical heat tracing and ceramic fiber insulation of the sample transport/sample introduction tube removed.
Figure 2:
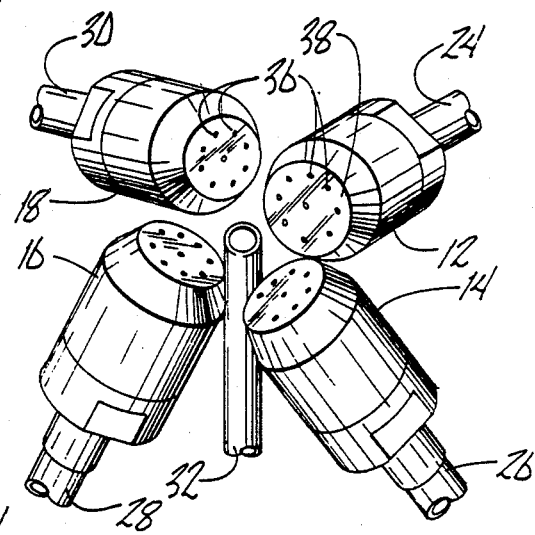
FIG. 2 is a close-up view of the nozzle portion of the system of this invention, showing the desired spacial arrangement which is preferred.
Figure 3:
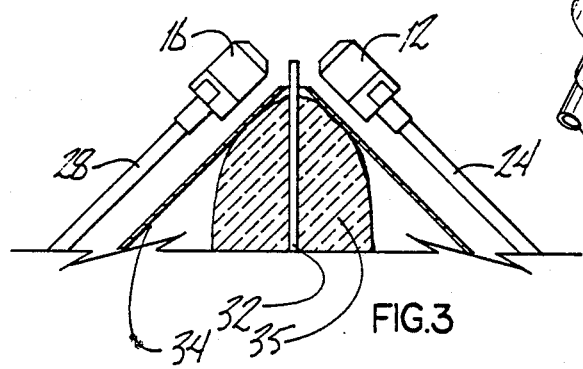
FIG. 3 shows the sample transport/sample introduction tube heat traced and insulated.
Figure 4:
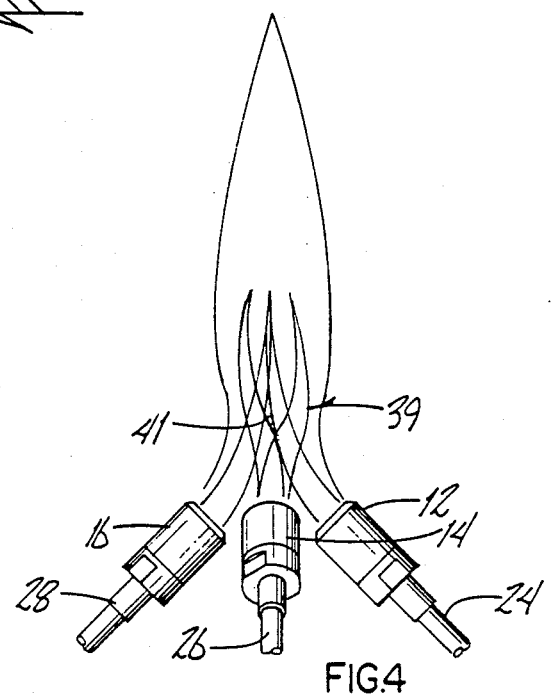
FIG. 4 shows the system of the present invention in use for spectrometric flame analysis.

As best seen in FIG. 3, stainless steel cone or hood 34 rests over the ceramic insulation in removable fashion. In the preferred form of this invention sample tube 32 is heat traced (not depicted). This refers to a heater, to heat the tube to prevent condensation. The heat traced sample tube is then wrapped with ceramic fiber insulation (FIG. 3 at 35). Nozzles 12, 14 16 and 18, respectively, have combustion gas exit holes 36 in nozzle head 38.

In the mode of operation as preferred, the flame atomization/excitation cell 39 is generated by the confluence of the flames produced by the combustion of propane and oxygen in the multiple nozzle burner assembly. Sample atomization in the flame is required for determination of the concentrations of the alkali elements in the sample stream.

The burner nozzles 12, 14, 16 and 18 are preferably arranged 90 degrees from each other and the axes of two opposite nozzles preferably subtend an angle of approximately 90 degrees. The axes of two opposite nozzles are in parallel planes, but are not necessarily coplanar. The distance between the planes for opposite nozzles is preferably approximately equal to the diameter of the combustion gas exit hole pattern 38 on the burner nozzles 12-18. If the distance between the planes of opposite burner nozzles is much smaller than the diameter of the combustion hole pattern 38, the sample stream is more quickly dispersed by the flames and a larger emission volume is produced. If the distance between the planes of opposite burner nozzles is much larger than the combustion hole pattern 38, then the interaction of the sample stream with the flames may be insufficient for atomization and excitation of the emission of the sample stream constituents. In that case, atomization and excitation of the sample constituents may be less than ideal, and the emission of characteristic radiation may not be sufficient for achieving optimum powers of detection. The diameter of the combustion hole pattern of the nozzles presently in use is approximately one centimeter; the offset distance is 1.25 cm. This is the presently known best mode.

Arrangement of the nozzles 12-18 on a wide base 20 of approximately 27 cm allows plenty of space for heat tracing and insulation of the sample transport/sample introduction tube 32 to within approximately 2 cm from its terminus, i.e., the point at which the sample stream leaves the confines of the sample introduction tube 32. In normal operation, it is preferred that at least the final 0.5 cm or so of the sample introduction tube 32 is in contact with the flames 39. Thus, degradation of sample stream temperature and the possibility of sample loss by condensation of vapor phase portions of the sample within the sample introduction tube can be prevented.

The use of the system 10 described here has been successful for the transport, introduction, atomization, and excitation of the emission spectra of sodium and potassium (without sample temperature degradation). This is necessary for determination of the concentrations of those elements in hot (up to 900° C.) vapor and particulate-containing sample streams produced in the fluidized bed combustion of coal. Implementations of the subject invention that employed stainless steel and quartz sample introduction tubes 32 have also been used for determinations of the concentration of sodium chloride vapor produced by the passage of known flows of nitrogen gas through a bed of solid sodium chloride maintained at known temperatures in the range of 500° C. to 715° C. The results of the latter determinations were in good agreement with the concentration values calculated from known vapor pressure data, and no loss of sodium chloride vapor was observed.

The multiple nozzle burner portion 12-18 of the apparatus 10 produces a flame atomization/excitation cell 39 in a manner that provides unsurpassed accessibility for introduction of a wide variety of materials into the axial channel 41 of the flame atomization/excitation cell. The configuration of the multiple nozzle burner portion of the apparatus 10 also provides a relatively large amount of working space immediately below the axial channel of the flame. For spectrometric analysis or monitoring, the lowest point of that channel, which begins at the confluence of the flames from the individual burner nozzles, is also the optimum point for introduction of materials into the flame atomization/excitation cell. The arrangement is therefore applicable for spectrometric examination and monitoring of material streams that may be introduced into the atomization/excitation cell by a variety of means that may or may not require use of the heat traced and insulated sample transport/sample introduction tube 32 for avoidance of sample stream temperature degradation. For example, a variety of devices suitable for the generation of liquid or aerosol streams from solutions, liquids, slurries, powders, or corrosive materials, could be placed directly below the flames, in place of the sample transport/sample introduction tube, and such devices could be operated in such a way that the momentum of the effluent material stream would be sufficient to accomplish introduction of material into the axial channel of the flame atomization/excitation cell. Some examples of such devices are: nebulizers, fluid bed aerosol generators, and thermo-spray devices.

Other envisioned applications are those in which introduction of material into the flame atomization/excitation cell is an essential element of a spectrometric analysis or monitoring approach for other material analysis techniques that employ material streams. Liquid chromatography and gas chromatography are two examples of such material analysis techniques.

Other possible applications of the system might employ a small furnace placed directly below the flames. The vapors produced from sample materials by operation of the furnace in ways commonly employed in chemical analysis procedures could be introduced into the axial channel of the flame atomization/excitation cell and could be analyzed without vapor loss due to condensation.

What is claimed is:

1. A spectral flame atomization and excitation system which provides high temperature gas streams for special analysis without degradation of sample stream by condensation losses, comprising:
   a manifold for supply of pre-mixed fuel gas and oxidant, said manifold being connected to at least two burner nozzles;
   a sample transport/sample introduction tube, generally vertically positioned and centrally positioned with respect to said burner nozzles;
   each of said burner nozzles being positioned symmetrically around said sample transport/sample introduction tube to provide an angularly disposed flame cell just at the exit end of said sample transport/sample introduction tube; and
   to provide space under said nozzles for heat tracing and insulation of said sample transport/sample introduction tube to minimize vapor loss.

2. The system of claim 1 wherein said sample transport/sample introduction tube is heat traced and insulated.

3. The system of claim 2 wherein a removable metal hood is positioned over said sample transport/sample introduction tube to act as a clean metal cover to prevent pickup of undesired adulterating particles which might be transferred to said flame for spectral analysis.

4. The system of claim 1 wherein said burners are arranged approximately 90° from each other.

5. The system of claim 4 wherein each nozzle contains a plurality of combustion gas exit holes arranged in a generally circular pattern which has a diameter, each opposite nozzle is in a plane and the distance between planes for opposite nozzles is preferably approximately equal to the diameter of the burner nozzle combustion gas exit hole pattern.

6. The system of claim 5 wherein the diameter of the combustion gas exit hole pattern for said nozzles is approximately 1 cm.

7. The system of claim 1 wherein said sample transport/sample introduction tube has a final or tip portion, said final or tip portion of said sample transport/sample introduction tube positioned with respect to said burner nozzles such that the tip portion is in contact with flames when said flame burner operates.

8. The system of claim 1 wherein approximately the last 0.5 cm. of the sample transport/sample introduction tube is in the flame cell.

9. A method of providing a flame and sample introduction means for the spectral analysis of high temperature gas streams without degradation of sample stream by condensation losses comprising:
   providing a composite stream of burning pre-mixed fuel gas and oxidant from at least two symmetrically positioned burner nozzle locations producing a flame cell, said locations being upwardly disposed at an angle to allow sufficient space beneath said nozzles to allow said sample transport/sample introduction tube to be treated to avoid vapor losses;
   feeding concentrically into said composite stream a hot gaseous stream of high temperature gas for spectral analysis;
   flame atomization and excitation of said high temperature gas stream in said composite stream of burning gas; treating said sample transport/sample introduction tube to prevent vapor loss; and
   spectrometrically analyzing said flame above the confluence of each of said symmetrically positioned flame streams to determine the composition of said sample stream.

10. The method of claim 9 wherein said nozzles are arranged approximately 90° from one another and wherein each nozzle contains a plurality of combustion gas exit holes arranged in a generally circular pattern, each opposite nozzle is in a plane and the distance between said planes for opposite nozzles is approximately equal to the diameter of said burner nozzle combustion gas exit hole pattern.

11. The method of claim 9 wherein approximately the last 0.5 cm. of the sample transport/sample introduction tube is placed within the flame cell.

12. The system of claim 11 wherein the sample is introduced into a furnace located below said flame cell, said furnace producing vapors from said sample which are introduced into said flame cell.

13. A spectral flame atomization and excitation system which provides introduction, atomization, and excitation of high temperature gas streams for spectral analysis by:
   a manifold for supply of pre-mixed fuel gas and oxidant, said manifold being connected to at least two burner nozzles;
   said burners arranged approximately 90° from each other;
   each nozzle containing a plurality of combustion gas exit holes arranged in a generally circular pattern;
   each of said nozzles are in a plane and the distance between planes for opposite nozzles is approximately equal to the diameter of the burner nozzle combustion gas exit hole pattern; and
   means for introducing samples into said flame cell.

* * * * *